United States Patent [19]
Yan et al.

[11] Patent Number: 5,641,749
[45] Date of Patent: Jun. 24, 1997

[54] METHOD FOR TREATING RETINAL GANGLION CELL INJURY USING GLIAL CELL LINE-DERIVED NEUROTHROPHIC FACTOR (GDNF) PROTEIN PRODUCT

[75] Inventors: Qiao Yan; Jean-Claude Louis, both of Thousand Oaks, Calif.

[73] Assignee: Amgen Inc., Thousand Oaks, Calif.

[21] Appl. No.: 564,458

[22] Filed: Nov. 29, 1995

[51] Int. Cl.$^6$ .................... A61K 47/00; A61K 31/685; A61F 2/00
[52] U.S. Cl. .................... 514/12; 435/69.1; 435/69.4
[58] Field of Search .................... 514/12; 435/69.4, 435/69.1

[56] References Cited

U.S. PATENT DOCUMENTS

| | | | |
|---|---|---|---|
| 3,981,303 | 9/1976 | Higuchi et al. | 128/260 |
| 3,986,510 | 10/1976 | Higuchi et al. | 128/260 |
| 3,995,635 | 12/1976 | Higuchi et al. | 128/260 |
| 4,188,373 | 2/1980 | Krezanosk | 128/260 |
| 4,217,898 | 8/1980 | Theeuwes | 424/78 |
| 4,474,452 | 10/1984 | Häslaai | 424/78 |
| 4,474,751 | 10/1984 | Haslam et al. | 424/78 |
| 4,474,752 | 10/1984 | Haslam et al. | 424/78 |
| 4,518,584 | 5/1985 | Mark et al. | 424/85.1 |
| 4,533,234 | 8/1985 | Wong | 424/427 |
| 4,853,224 | 8/1989 | Wong | 424/427 |
| 4,863,457 | 9/1989 | Lee | 424/428 |
| 4,865,846 | 9/1989 | Kaufman | 424/428 |
| 4,882,150 | 11/1989 | Kaufman | 424/428 |
| 4,892,538 | 1/1990 | Aebischer et al. | 604/89.1 |
| 5,011,472 | 4/1991 | Aebischer et al. | 604/892.1 |
| 5,106,627 | 4/1992 | Aebischer et al. | 530/399 |
| 5,221,696 | 6/1993 | Ke et al. | 514/786 |
| 5,252,714 | 10/1993 | Harris et al. | 530/391.9 |
| 5,384,333 | 1/1995 | Davis et al. | 424/405 |
| 5,422,116 | 6/1995 | Yen et al. | 424/427 |

FOREIGN PATENT DOCUMENTS

| | | |
|---|---|---|
| 154316 | 9/1985 | European Pat. Off. . |
| 401384 | 12/1990 | European Pat. Off. . |
| 423980 | 4/1991 | European Pat. Off. . |
| WO91/10425 | 7/1991 | WIPO . |
| WO91/10470 | 7/1991 | WIPO . |
| WO93/06116 | 4/1993 | WIPO . |
| WO93/15608 | 8/1993 | WIPO . |

OTHER PUBLICATIONS

Malik et al., "TGF-13 Superfamily Members promote Survival of Midgrain Depaminergic Neurons and Protect Them Against MPP+ Toxicity", EMSO Journal, vol. 14 (4) pp. 736–742 (1995).

M. S. Silverman and E. S. Hughes, "Tranplantation of Photoreceptors to Light Damaged Retinas", Investigative Opthamology and Visual Science, vol. 3/8, Aug., pp. 1684–1690 (1989).

Aebischer et al. (1991), 'Long–Term Cross–Species Brain Transplantation of a Polymer–Encapsulated Dopamine–Secreting Cell Line', Exper. Neurol. 111:269–275.

Beck et al. (1995), 'Mesencephalic dopaminergic neurons protected by GDNF from axotomy–induced degeneration in the adult brain', Nature 373:339–341.

Bothwell (1995), 'Functional Interactions of Neurotrophins and Neurotrophin Receptors', Ann., Rev. Neurosci. 18:223–253.

Chamow et al. (1994), 'Modification of CD4 Immunoadhesin with Monomethoxypoly (ethylene glycol) Aldehyde via Reductive Alkylation', Bioconjugate Chem. 5:133–140.

Chao et al. (1995) 'p75 and Trk: a two–receptor system', TINS 18:321–326.

Cunningham and Wells (1989), 'High–Resolution Epitope Mapping of hGH–Receptor Interactions by Alanine–Scanning Mutagenesis', Science 244:1081–1085.

Dayhoff (1972), Atlas of Protein Sequence and Structure 5:124.

Francis (1992), 'Protein modification and fusion proteins', Focus on Growth Factors 3(2):4–10.

Gurny, R. et al. (1987), 'Design and Evaluation of Controlled Release Systems For The Eye', Journal of Controlled Release 6:367–373.

Hefti (1994), 'Neurotrophic Factor Therapy for Nervous Sytem Degenerative Diseases', J. Neurobiol. 25:1418–1435.

Henderson et al. (1994), 'GDNF: A Potent Survival Factor for Motoneurons Present in Peripheral Nerve and Muscle', Science 266:1062–1064.

Hoffer et al. (1994), 'Glial cell line–derived neurotrophic factor reverses toxin–induced injury to midbrain dopaminergic neurons in vivo', Neurosci. Lett. 182:107–111.

Hudson et al. (1995), 'Glial Cell Line–derived Neurotrophic Factor Augments Midbrain Dopaminergic Circuits In Vivo', Brain Res. Bull. 36:425–432.

Kastner et al. (1994), 'Glial cell–line derived neurotrophic factor (GDNF) mRNA upregulation in striatum and cortical areas after pilocarpine–induced status epilepticus in rats', Mol. Brain Res. 26:325–330.

Krieglstein et al. (1995), 'TGF–β superfamily members promote survival of midbrain dopaminergic neurons and protect them against MPP+ toxicity', EMBO J. 14:736–742.

Lehwalder et al. (1989), 'Rapid Communication Survival of Purified Embryonic Chick Retinal Ganglion Cells in the Presence of Neurotrophic Factors', J. Neurosci. Res. 24:329–337.

Leifer et al. (1991), 'Brief Communication Immunofluorescent Characterization of Retinal Ganglion Cell Neurites Cultures on Substrates Coated with Antibodies against Thy–1', Exp. Neurol. 113:386–390.

(List continued on next page.)

Primary Examiner—Howard E. Schain
Assistant Examiner—P. L. Touzeau
Attorney, Agent, or Firm—Daniel R. Curry; Ron K. Levy; Steven M. Odre

[57] ABSTRACT

The present invention relates generally to methods for treating injury or degeneration of retinal ganglion cells by administering glial cell line-derived neurotrophic factor (GDNF). The invention relates specifically to methods for treating optic nerve injury or degeneration associated with glaucoma.

20 Claims, No Drawings

OTHER PUBLICATIONS

Lin et al. (1993), 'GDNF: A Glial Cell Line–Derived Neurotrophic Factor for Midbrain Dopaminergic Neurons', *Science* 260:1130–1132.

Louis et al. (1992), 'Receptor–Mediated Toxicity of Norepinephrine on Cultured Catecholaminergic Neurons of the Rat Brain Stem[1]', *J. Pharmacol. Exp. Therap.* 262:1274–1283.

Louis et al. (1993), 'CNTF Protection of Oligodendrocytes Against Natural and Tumor Necrosis Factor–Induced Death', *Science* 259:689–692.

Malik et al. (1992), 'Polyethylene Glycol (PEG)–modified Granulocyte–Macrophage Colony–stimulating Factor (GM–CSF) with Conserved Biological Activity', *Exp. Hematol.* 20:1028–1035.

Mansour–Robaey et al. (1994), 'Effects of ocular injury and administration of brain–derived neurotrophic factor on survival and regrowth of axotomized retinal ganglion cells', *Proc. Natl. Acad. Sci* 91:1632–1636.

Matheson et al. (1995), 'The In Vivo Responses of Neonatal Rat Dorsal Root Ganglion Neurons to Neurotrophins and GDNF', *Soc. Neurosci. Abstr.* 21:544.

Oppenheim et al. (1995), 'Developing motor neurons rescued from programmed and axotomy–induced cell death by GDNF', *Nature* 373:344–346.

Poulsen et al. (1994), 'TGFβ2 and TGFβ3 Are Potent Survival Factors for Midbrain Dopaminergic Neurons', *Neuron* 13:1245–1252.

Schaar et al. (1994), 'Multiple Astrocyte Transcripts Encode Nigral Trophic Factors in Rat and Human', *Exp. Neurol.* 130:387–393.

Schaar et al. (1993), 'Regional and Cell–Specific Expression of GDNF in Rat Brain', *Exp. Neurol.* 124:368–371.

Snider (1994), 'Functions of the Neurotrophins during Nervous System Development: What the Knockouts Are Teaching Us', *Cell* 77:627–638.

Theonen et al. (1985), 'Neurotrophic Factors', *Science* 229:238–242.

Thoenen (1991), 'The changing scene of neurotrophic factors', *Trends. Neurosci.* 14:165–170.

Tomac et al. (1995), 'Protection and repair of the nigrostriatal dopaminergic system by GDNF in vivo', *Nature* 373:335–339.

Tresco et al. (1992), 'Polymer Encapsulated Neurotransmitter Secreting Cells', *ASAIO* 38:17–23.

Trupp et al. (1995), 'Peripheral Expression and Biological Activities of GDNF, a New Neurotrophic Factor for Avian and Mammalian Peripheral Neurons', *J. Cell Biol.* 130:137–148.

Varon et al. (1978), 'Trophic Mechanisms in the Peripheral Nervous System', *Ann. Rev. Neuroscience* 1:327–361.

Winn et al. (1991), 'Behavioral Recovery following Intrastriatal Implantation of Microencapsulated PC12 Cells', *Exper. Neurol.* 113:322–329.

Yan et al. (1993), 'Influences of Neorotrophins on Mammalian Motoneurons in vivo', *J. Neurobiol.* 24:1555–77.

Yan and Matheson (1995), 'In vivo neurotrophic effects of GDNF on neonatal and adult facial motor neurons', *Nature* 373:341–344.

Zurn et al. (1994), 'Glial cell–line derived neurotrophic factor (GDNF), a new neurotrophic factor for motoneurones', *Neuroreport* 6:113–118.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 134 amino acid residues
        ( B ) TYPE: amino acid
        ( D ) TOPOLOGY: linear ( i x ) FEATURE:

( A ) NAME/KEY: inferred amino acid sequence for mature human GDNF ( x i ) SEQUENCE DESCRIPTION: SEQ ID NO:1:

```
Ser Pro Asp Lys Gln Met Ala Val Leu Pro Arg Arg Glu Arg Asn Arg
 1               5                  10                      15

Gln Ala Ala Ala Ala Asn Pro Glu Asn Ser Arg Gly Lys Gly Arg Arg
             20                  25                  30

Gly Gln Arg Gly Lys Asn Arg Gly Cys Val Leu Thr Ala Ile His Leu
         35                  40                  45

Asn Val Thr Asp Leu Gly Leu Gly Tyr Glu Thr Lys Glu Glu Leu Ile
     50                  55              60

Phe Arg Tyr Cys Ser Gly Ser Cys Asp Ala Ala Glu Thr Thr Tyr Asp
 65              70                  75                      80

Lys Ile Leu Lys Asn Leu Ser Arg Asn Arg Arg Leu Val Ser Asp Lys
                 85                  90                  95

Val Gly Gln Ala Cys Cys Arg Pro Ile Ala Phe Asp Asp Asp Leu Ser
             100                 105             110

Phe Leu Asp Asp Asn Leu Val Tyr His Ile Leu Arg Lys His Ser Ala
         115                 120                 125

Lys Arg Cys Gly Cys Ile
     130
```

METHOD FOR TREATING RETINAL GANGLION CELL INJURY USING GLIAL CELL LINE-DERIVED NEUROTHROPHIC FACTOR (GDNF) PROTEIN PRODUCT

BACKGROUND OF THE INVENTION

The present invention relates generally to methods for treating injury or degeneration of retinal ganglion cells by administering glial cell line-derived neurotrophic factor (GDNF) protein product. The invention relates specifically to methods for treating glaucoma or other diseases/conditions involving retinal ganglion cell degeneration.

Neurotrophic factors are natural proteins, found in the nervous system or in non-nerve tissues innervated by the nervous system, that function to promote the survival and maintain the phenotypic differentiation of certain nerve and/or glial cell populations (Varon et al., Ann. Rev. Neuroscience, 1:327, 1979; Thoenen et al., Science, 229:238, 1985). Because of this physiological role, neurotrophic factors are useful in treating the degeneration of such nerve cells and the loss of differentiated function that results from nerve damage. Nerve damage is caused by conditions that compromise the survival and/or proper function of one or more types of nerve cells, including: (1) physical injury, which causes the degeneration of the axonal processes (which in turn causes nerve cell death) and/or nerve cell bodies near the site of injury, (2) temporary or permanent cessation of blood flow (ischemia) to parts of the nervous system, as in stroke, (3) intentional or accidental exposure to neurotoxins, such as the cancer and AIDS chemotherapeutic agents cisplatinum and dideoxycytidine, respectively, (4) chronic metabolic diseases, such as diabetes or renal dysfunction, or (5) neurodegenerative diseases such as Parkinson's disease, Alzheimer's disease, and Amyotrophic Lateral Sclerosis, which result from the degeneration of specific neuronal populations. In order for a particular neurotrophic factor to be potentially useful in treating nerve damage, the class or classes of damaged nerve cells must be responsive to the factor. It has been established that all neuron populations are not responsive to or equally affected by all neurotrophic factors.

The first neurotrophic factor to be identified was nerve growth factor (NGF). NGF is the first member of a defined family of trophic factors, called the neurotrophins, that currently includes brain-derived neurotrophic factor (BDNF), neurotrophin-3 (NT-3), NT-4/5, and NT-6 (Thoenen, Trends. Neurosci., 14:165–170, 1991; Snider, Cell, 77:627–638, 1994; Bothwell, Ann. Rev. Neurosci, 18:223–253, 1995). These neurotrophins are known to act via the family of trk tyrosine kinase receptors, i.e., trkA, trkB, trkC, and the low affinity p75 receptor (Snider, Cell, 77:627–638, 1994; Bothwell, Ann. Rev. Neurosci, 18:223–253, 1995; Chao et al., TINS 18:321–326, 1995).

Glial cell line-derived neurotrophic factor (GDNF) is a recently discovered protein identified and purified using assays based upon its efficacy in promoting the survival and stimulating the transmitter phenotype of mesencephalic dopaminergic neurons in vitro (Lin et al., Science, 260:1130–1132, 1993). GDNF is a glycosylated disulfide-bonded homodimer that has some structural homology to the transforming growth factor-beta (TGF-β) super family of proteins (Linet al., Science, 260:1130–1132, 1993; Krieglstein et al., EMBO J., 14:736–742, 1995; Poulsen et al., Neuron, 13:1245–1252, 1994). GDNF mRNA has been detected in muscle and Schwann cells in the peripheral nervous system (Henderson et al., Science, 266:1062–1064, 1994; Trupp et al., J. Cell Biol., 130:137–148, 1995) and in type I astrocytes in the central nervous system (Schaar et al., Exp. Neurol., 124:368–371, 1993). In vivo, treatment with exogenous GDNF stimulates the dopaminergic phenotype of substantia nigra neurons and restores functional deficits induced by axotomy or dopaminergic neurotoxins in animal models of Parkinson's disease (Hudson et al., Brain Res. Bull., 36:425–432, 1995; Beck et al., Nature, 373:339–341, 1995; Tomac et al., Nature, 373:335–339, 1995; Hoffer et al., Neurosci. Lett., 182:107–111, 1994). Although originally thought to be relatively specific for dopaminergic neurons, at least in vitro, evidence is beginning to emerge indicating that GDNF may have a larger spectrum of neurotrophic targets besides mesencephalic dopaminergic and somatic motor neurons (Yan and Matheson, Nature 373:341–344, 1995; Oppenheimet al., Nature, 373:344–346, 1995; Matheson et al., Soc. Neurosci. Abstr, 21, 544, 1995; Trupp et al., J. Cell Biol., 130:137–148, 1995). In particular, GDNF was found to have neurotrophic efficacy on brainstem and spinal cord cholinergic motor neurons, both in vivo and in vitro (Oppenheim et al., Nature, 373:344–346, 1995; Zurn et al., Neuroreport, 6:113–118, 1994; Yan et al., Nature, 373: 341–344, 1995; Henderson et al., Science, 266:1062–1064, 1994).

Of general interest to the present invention is WO93/06116 (Lin et al., Syntex-Synergen Neuroscience Joint Venture), published Apr. 1, 1993, which reports that GDNF is useful for the treatment of nerve injury, including injury associated with Parkinson's disease. Also of interest are a report in Schmidt-Kastner et al., Mol. Brain Res., 26:325–330, 1994 that GDNF mRNA became detectable and was upregulated after pilocarpine-induced seizures; reports in Schaar et al., Exp. Neurol., 124:368–371, 1993 and Schaar et al., Exp. Neurol., 130:387–393, 1994 that basal forebrain astrocytes expressed moderate levels of GDNF mRNA under culture conditions, but that GDNF did not alter basal forebrain ChAT activity; and a report in currently pending U.S. application Ser. No. 08/535,682 filed Sep. 28, 1995 that GDNF is useful for treating injury or degeneration of basal forebrain cholinergic neurons. GDNF has not previously been shown to promote survival or regeneration of injured retinal ganglion cells.

Retinal ganglion cells play a major role in visual perception, which occurs in several stages. First, light is converted into electrical signals by specialized neurons, called photoreceptors, which are located in the outer layers of the retina. These signals are then combined and transmitted by interneurons to the retinal ganglion cells, located in the inner layer of the retina, which then relay this information to the visual cortex region of the brain. The retinal ganglion cell axons converge to form the optic nerve, which projects to the lateral geniculate nucleus and to the superior colliculus in the brain, as well as to brainstem nuclei.

Damage to retinal ganglion cells is the primary injury seen in glaucoma, which is the third most prevalent cause of blindness. Glaucoma is the term used for a group of disorders characterized by an optic neuropathy involving the progressive loss of retinal ganglion cells. This damage to retinal ganglion cells is characterized by axonal transport dysfunction and histopathologic abnormalities of the axons within the optic nerve head, and is associated with a typically excavated appearance of the optic nerve head. Optic nerve degeneration can also result from other conditions of the optic disc, e.g., papilledema due to increased intracranial pressure, papillitis (a form of optic neuritis) or ischemia.

In most cases of glaucoma, the optic nerve damage is caused by elevated intraocular pressure. The major types of glaucoma associated with elevated intraocular pressure are open-angle, angle-closure and secondary glaucomas. In some cases of glaucoma, a similar excavation of the nerve head occurs despite a normal intraocular pressure range. In all cases, higher intraocular pressures are generally associated with greater nerve damage. Glaucoma is usually treated by attempting to lower the intraocular pressure, either medically or surgically.

Chronic open-angle glaucoma is the most common type and is seen in about 0.5% of American and European adults. In this type of glaucoma, there is a blockage to the resorption of aqueous humor inside the eye, causing the intraocular pressure to rise above its normal maximum of 21 mm Hg and to gradually destroy the axons and supporting tissue in the optic disc. This type of glaucoma is ordinarily asymptomatic until well advanced. Initial visual loss is seen in the peripheral field of vision. Diagnosis is made by measurements of intraocular pressure, examination of the optic disc, and testing of the patient's visual fields. Treatment is primarily medical, by topical administration of parasympathomimetics (pilocarpine and carbachol), beta-adrenergic blockers (timolol) and sympathomimetics (epinephrine) which act to decrease intraocular pressure. When these medications, individually or in combination, no longer arrest the progressive damage, indirect parasympathomimetics (echothiophate) and carbonic anhydrase inhibitors (acetazolamide and methazolamide) are prescribed. If medical therapy fails, surgical treatment can be performed to open outflow channels. A subset of open-angle glaucoma is congenital, resulting from the developmental failure of certain anatomical structures in the eye.

In angle-closure glaucoma, the outflow of aqueous humor is mechanically impeded owing to a shallow anterior chamber. The intraocular pressure remains normal until a pupillary block (causing resistance to aqueous flow through the pupil) obstructs the resorptive surfaces in the angle. The pressure then rises precipitously, often to above 50 mm Hg. This glaucoma is generally monocular and is characterized by a red and painful eye, a fixed and dilated pupil, decreased vision, sweating and nausea. An acute attack is a medical emergency and is treated with parenteral acetazolamide, oral glycerol or intravenous mannitol, and topical administration of pilocarpine and sometimes timolol. After the acute attack is managed, the anatomic problem can be eliminated by surgery.

Secondary glaucoma develops as a consequence of another ocular disease. Examples are glaucoma precipitated by swelling of the lens, neovascularization (formation of new blood vessels) in the angle structures, chronic inflammation, or severe blunt trauma to angle structures. The treatment for secondary lens-induced glaucoma is surgical removal of the lens. Most other secondary glaucomas are managed medically in the same way as primary open-angle glaucoma. Neovascular glaucoma is difficult to treat, but may be improved with laser photocoagulation.

There continues to exist a need for methods and therapeutic compositions useful for the treatment of retinal ganglion cell injury associated with conditions such as glaucoma. Such methods and therapeutic compositions would ideally protect the retinal ganglion cells and optic nerve from progressive injury and promote survival or regeneration of the damaged neurons, without severe adverse side effects.

SUMMARY OF THE INVENTION

The present invention provides methods for treating injury or degeneration of retinal ganglion cells by administering a therapeutically effective amount of glial cell line-derived neurotrophic factor (GDNF) protein product. According to one specific aspect of the invention, methods are provided for treating glaucoma by administering a therapeutically effective amount of GDNF protein product. In another aspect, methods are provided for treating injury or degeneration of the optic nerve due to conditions affecting the optic nerve head such as glaucoma, papilledema, papillitis and ischemia. A therapeutically effective amount GDNF protein product is administered to promote the survival or regeneration of retinal ganglion cell axons forming the optic nerve. It is contemplated that such GDNF protein products would include a GDNF protein such as that depicted by the amino acid sequence set forth in SEQ ID NO:1, as well as variants and derivatives thereof. The present invention is based on the discovery that retinal ganglion cells selectively take up and retrogradely transport GDNF protein product and that GDNF promotes the survival of retinal ganglion cells in vitro, and the discovery that GDNF promotes the survival of injured retinal ganglion cells in vivo, i.e., the main population of neurons damaged in glaucoma.

According to the invention, the GDNF protein product may be administered parenterally at a dose ranging from about 1 µg/kg/day to about 100 mg/kg/day, typically at a dose of about 0.1 mg/kg/day to about 25 mg/kg/day, and usually at a dose of about 5 mg/kg/day to about 20 mg/kg/day. It is also contemplated that, depending on the individual patient's needs and route of administration, the GDNF protein product may be given at a lower frequency such as weekly or several times per week, rather than daily. It is further contemplated that GDNF protein product may be administered directly intraocularly. One skilled in the art will appreciate that with such intraocular administration a smaller amount of GDNF protein product may be used, for example, an intraocular dose in the range of about 1 µg/eye to about 1 mg/eye in a single injection or in multiple injections. It is further contemplated that GDNF protein product be administered in combination or conjunction with an effective amount of a second therapeutic agent for glaucoma.

The invention also provides for the use of GDNF protein product in the manufacture of a medicament or pharmaceutical composition for the treatment of injury or degeneration of retinal ganglion cells, including the treatment of glaucoma. Such pharmaceutical compositions include topical, oral or parenteral GDNF protein product formulations. It will also be appreciated by those skilled in the art that the administration process can be accomplished via cell therapy and gene therapy means, as further described below. Numerous additional aspects and advantages of the invention will become apparent to those skilled in the art upon consideration of the following detailed description of the invention which describes presently preferred embodiments thereof.

DETAILED DESCRIPTION OF THE INVENTION

The present invention provides a method for treating injury or degeneration of retinal ganglion cells by administering a therapeutically effective amount of glial cell line-derived neurotrophic factor (GDNF) protein product. According to one aspect of the invention, methods are provided for treating retinal ganglion cell degeneration due to glaucoma by administering a therapeutically effective amount of GDNF protein product by means of a pharmaceutical composition, the implantation of GDNF-expressing cells, or GDNF gene therapy. The invention may be practiced using any biologically active GDNF protein product, including a GDNF protein represented by the amino acid sequence set forth in SEQ ID NO:1, including variants and derivatives thereof. In addition to oral, parenteral or topical delivery of the GDNF protein product, administration via cell therapy and gene therapy procedures is contemplated.

The present invention is based on the initial discoveries that GDNF promotes the survival of retinal ganglion cells in culture and that retinal ganglion cells selectively take up and retrogradely transport GDNF in a receptor-specific fashion. It was then determined that GDNF plays a role in the development, survival and maintenance of function of these neurons. In addition, the invention is based on the discovery that GDNF protein product increases the in vivo survival of injured retinal ganglion cells, which cells make up the main population of neurons damaged in glaucoma. It is postulated that administration of exogenous GDNF protein product will protect retinal ganglion cells from traumatic damage or from damage resulting from a lack of neurotrophic factors caused by interruption of transport of the factors from the axon to the cell body. Such treatment is expected to allow retinal ganglion cells to tolerate intermittent insults from either eye pressure, poor vascular nutrition or other circumstances which might otherwise cause glaucoma or other optic nerve diseases, and to preserve the functional integrity of the optic nerve.

According to the invention, the GDNF protein product may be administered parenterally at a dose ranging from about 1 µg/kg/day to about 100 mg/kg/day, typically at a dose of about 0.1 mg/kg/day to about 25 mg/kg/day, and usually at a dose of about 5 mg/kg/day to about 20 mg/kg/day. GDNF protein product may be administered directly intraocularly. In such cases, a smaller amount of GDNF protein product will be administered, for example, from about 1 µg/eye to about 1 mg/eye in a single injection or in multiple injections. GDNF may also be administered in the subretinal space between the photoreceptor layer and retinal pigmentosa epithelial layers. It is further contemplated that GDNF protein product be administered with an effective amount of a second therapeutic agent for the treatment of glaucoma. Such second agents would include, e.g., parasympathomimetics (pilocarpine and carbachol), beta-adrenergic blockers (timolol), sympathomimetics (epinephrine), indirect parasympathomimetics (echothiophate) and carbonic anhydrase inhibitors (acetazolamide and methazolamide). The invention also provides for the use of GDNF protein product in preparation of a medicament for the treatment of injury or degeneration of retinal ganglion cells, including the treatment of glaucoma. A variety of pharmaceutical formulations and different delivery techniques are described in further detail below.

As used herein, the term "GDNF protein product" includes purified natural, synthetic or recombinant glial cell line-derived neurotrophic factor, biologically active GDNF variants (including insertion, substitution and deletion variants), and chemically modified derivatives thereof. Also included are GDNFs that are substantially homologous to the human GDNF having the amino acid sequence set forth in SEQ ID NO:1. GDNF protein products may exist as homodimers or heterodimers in their biologically active form.

The term "biologically active" as used herein means that the GDNF protein product demonstrates similar neurotrophic properties, but not necessarily all of the same properties, and not necessarily to the same degree, as the GDNF having the amino acid sequence set forth in SEQ ID NO:1. The selection of the particular neurotrophic properties of interest depends upon the use for which the GDNF protein product is being administered.

The term "substantially homologous" as used herein means having a degree of homology to the GDNF having the amino acid sequence set forth in SEQ ID NO:1 that is preferably in excess of 70%, most preferably in excess of 80%, and even more preferably in excess of 90% or 95%. For example, the degree of homology between the rat and the human protein is about 93%, and it is contemplated that preferred mammalian GDNF will have a similarly high degree of homology. The percentage of homology as described herein is calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in *Atlas of Protein Sequence and Structure*, Vol. 5, p. 124, National Biochemical Research Foundation, Washington, D.C. (1972), the disclosure of which is hereby incorporated by reference). Also included as substantially homologous is any GDNF protein product which may be isolated by virtue of cross-reactivity with antibodies to the GDNF of SEQ ID NO:1 or whose genes may be isolated through hybridization with the gene or with segments of the gene encoding the GDNF of SEQ ID NO:1.

The GDNF protein products according to this invention may be isolated or generated by any means known to those skilled in the art. Exemplary methods for producing GDNF protein products useful in the present invention are described in U.S. application Ser. No. 08/182,183 filed May 23, 1994 and its parent applications; PCT Application No. PCT/US92/07888 filed Sep. 17, 1992, published as WO 93/06116 (Lin et al., Syntex-Synergen Neuroscience Joint Venture); European Patent Application No. 92921022.7, published as EP 610 254; and co-owned, co-pending U.S. application Ser. No. 08/535,681 filed Sep. 28, 1995 ("Truncated Glial Cell-Line Derived Neurotrophic Factor"), the disclosures of which are hereby incorporated by reference.

Naturally-occurring GDNF protein products may be isolated from mammalian neuronal cell preparations, or from a mammalian cell line secreting or expressing GDNF. For example, WO93/06116 describes the isolation of GDNF from serum-free growth conditioned medium of B49 glioblastoma cells. GDNF protein products may also be chemically synthesized by any means known to those skilled in the art. GDNF protein products are preferably produced via recombinant techniques because they are capable of achieving comparatively higher amounts of protein at greater purity. Recombinant GDNF protein product forms include glycosylated and non-glycosylated forms of the protein, and protein expressed in bacterial, mammalian or insect cell systems.

In general, recombinant techniques involve isolating the genes responsible for coding GDNF, cloning the gene in suitable vectors and cell types, modifying the gene if necessary to encode a desired variant, and expressing the gene in order to produce the GDNF protein product. Alternatively, a nucleotide sequence encoding the desired GDNF protein product may be chemically synthesized. It is contemplated that GDNF protein product may be expressed using nucleotide sequences which differ in codon usage due to the degeneracies of the genetic code or allelic variations. WO93/06116 describes the isolation and sequencing of a cDNA clone of the rat GDNF gene, and the isolation, sequencing and expression of a genomic DNA clone of the human GDNF gene. WO93/06116 also describes vectors, host cells, and culture growth conditions for the expression of GDNF protein product. Additional vectors suitable for the expression of GDNF protein product in *E. coli* are disclosed in published European Patent Application No. EP 0 423 980 ("Stem Cell Factor") published Apr. 24, 1991, the disclosure of which is hereby incorporated by reference. The DNA sequence of the gene coding for mature human GDNF and the amino acid sequence of the GDNF is shown in FIG. 19 (SEQ ID NO:5) of WO93/06116. FIG. 19 does not show the entire coding sequence for the pre-pro portion of GDNF, but the first 50 amino acids of human pre-pro GDNF are shown in FIG. 22 (SEQ ID NO:8) of WO93/06116.

Naturally-occurring GDNF is a disulfide-bonded dimer in its biologically active form. The material isolated after expression in a bacterial system is essentially biologically inactive, and exists as a monomer. Refolding is necessary to produce the biologically active disulfide-bonded dimer. Processes for the refolding and naturation of the GDNF expressed in bacterial systems are described in WO93/06116. Standard in vitro assays for the determination of GDNF activity are described in WO93/06116 and in co-owned, co-pending U.S. application Ser. No. 08/535,681 filed Sep. 28, 1995, and are hereby incorporated by reference.

A. GDNF Variants

The term "GDNF variants" as used herein includes polypeptides in which amino acids have been deleted from ("deletion variants"), inserted into ("addition variants"), or substituted for ("substitution variants"), residues within the amino acid sequence of naturally-occurring GDNF. Such variants are prepared by introducing appropriate nucleotide changes into the DNA encoding the polypeptide or by in vitro chemical synthesis of the desired polypeptide. It will be appreciated by those skilled in the art that many combinations of deletions, insertions, and substitutions can be made provided that the final molecule possesses GDNF biological activity.

Mutagenesis techniques for the replacement, insertion or deletion of one or more selected amino acid residues are well known to one skilled in the art (e.g., U.S. Pat. No. 4,518,584, the disclosure of which is hereby incorporated by reference.) There are two principal variables in the construction of variants: the location of the mutation site and the nature of the mutation. In designing GDNF variants, the selection of the mutation site and nature of the mutation will depend on the GDNF characteristic(s) to be modified. The sites for mutation can be modified individually or in series, e.g., by (1) substituting first with conservative amino acid choices and then with more radical selections depending upon the results achieved, (2)deleting the target amino acid residue, or (3) inserting amino acid residues adjacent to the located site. Conservative changes in from 1 to 20 amino acids are preferred. Once the amino acid sequence of the desired GDNF protein product is determined, the nucleic acid sequence to be used in the expression of the protein is readily determined. N-terminal and C-terminal deletion variants may also be generated by proteolytic enzymes.

For GDNF deletion variants, deletions generally range from about 1 to 30 residues, more usually from about 1 to 10 residues, and typically from about 1 to 5 contiguous residues. N-terminal, C-terminal and internal intrasequence deletions are contemplated. Deletions may be introduced into regions of low homology with other TGF-β super family members to modify the activity of GDNF. Deletions in areas of substantial homology with other TGF-β super family sequences will be more likely to modify the GDNF biological activity more significantly. The number of con-secutive deletions will be selected so as to preserve the tertiary structure of the GDNF protein product in the affected domain, e.g., cysteine crosslinking. Non-limiting examples of deletion variants include truncated GDNF protein products lacking from one to forty N-terminal amino acids of GDNF, or variants lacking the C-terminal residue of GDNF, or combinations thereof, as described in co-owned, co-pending U.S. application Ser. No. 08/535,681 filed Sep. 28, 1995, which is hereby incorporated by reference.

For GDNF addition variants, amino acid sequence additions typically include N-and/or C-terminal fusions ranging in length from one residue to polypeptides containing a hundred or more residues, as well as internal intrasequence additions of single or multiple amino acid residues. Internal additions may range generally from about 1 to 10 residues, more typically from about 1 to 5 residues, and usually from about 1 to 3 amino acid residues. Examples of N-terminal addition variants include GDNF with an N-terminal methionyl residue (an artifact of the direct expression of GDNF in bacterial recombinant cell culture), which is designated [Met$^{-1}$]GDNF, and fusion of a heterologous N-terminal signal sequence to the N-terminus of GDNF to facilitate the secretion of mature GDNF from recombinant host cells. Such signal sequences generally will be obtained from, and thus be homologous to, the intended host cell species. Additions may also include amino acid sequences derived from the sequence of other neurotrophic factors. A preferred GDNF protein product for use according to the present invention is the recombinant human [Met$^{-1}$]GDNF.

GDNF substitution variants have at least one amino acid residue of the GDNF amino acid sequence removed and a different residue inserted in its place. Such substitution variants include allelic variants, which are characterized by naturally-occurring nucleotide sequence changes in the species population that may or may not result in an amino acid change. Examples of substitution variants (see, e.g., SEQ ID NO: 50) are disclosed in co-owned, co-pending U.S. application Ser. No. 08/535,681 filed Sep. 28, 1995, and are hereby incorporated by reference.

Specific mutations of the GDNF amino acid sequence may involve modifications to a glycosylation site (e.g., serine, threonine, or asparagine). The absence of glycosylation or only partial glycosylation results from amino acid substitution or deletion at any asparagine-linked glycosylation recognition site or at any site of the molecule that is modified by addition of an O-linked carbohydrate. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. A variety of amino acid substitutions or deletions at one or both of the first or third amino acid positions of a glycosylation recognition site (and/or amino acid deletion at the second position) result in non-glycosylation at the modified tripeptide sequence. Thus, the expression of appropriate altered nucleotide sequences produces variants which are not glycosylated at that site. Alternatively, the GDNF amino acid sequence may be modified to add glycosylation sites.

One method for identifying GDNF amino acid residues or regions for mutagenesis is called "alanine scanning mutagenesis" as described by Cunningham and Wells (*Science*, 244:1081–1085, 1989). In this method, an amino acid residue or group of target residues are identified (e.g., charged residues such as Arg, Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing additional or alternate residues at the sites of substitution. Thus, the target site for introducing an amino acid sequence variation is determined, alanine scanning or random mutagenesis is conducted on the corresponding target codon or region of the DNA sequence, and the expressed GDNF variants are screened for the optimal combination of desired activity and degree of activity.

The sites of greatest interest for substitutional mutagenesis include sites where the amino acids found in GDNF proteins from various species are substantially different in terms of side-chain bulk, charge, and/or hydrophobicity. Other sites of interest are those in which particular residues of GDNF-like proteins, obtained from various species, are identical. Such positions are generally important for the biological activity of a protein. Initially, these sites are substituted in a relatively conservative manner. Such conservative substitutions are shown in Table 1 under the heading of preferred substitutions. If such substitutions result in a change in biological activity, then more substantial changes (exemplary substitutions) are introduced, and/or other additions or deletions may be made, and the resulting products screened for activity.

TABLE 1

Amino Acid Substitutions

| Original Residue | Preferred Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

Conservative modifications to the amino acid sequence (and the corresponding modifications to the encoding nucleic acid sequences) are expected to produce GDNF protein products having functional and chemical characteristics similar to those of natural GDNF. In contrast, substantial modifications in the functional and/or chemical characteristics of GDNF protein products may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for another. Such substituted residues may be introduced into regions of the GDNF protein that are homologous with other TGF-β super family proteins, or into the non-homologous regions of the molecule.

B. GDNF Derivatives

Chemically modified derivatives of GDNF or GDNF variants may be prepared by one of skill in the art given the disclosures herein. The chemical moieties most suitable for derivatization include water soluble polymers. A water soluble polymer is desirable because the protein to which it is attached does not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization may be ascertained by administering the derivative, in the desired form (i.e., by osmotic pump, or, more preferably, by injection or infusion, or, further formulated for oral, pulmonary or other delivery routes), and determining its effectiveness.

Suitable water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or unbranched. For polyethylene glycol, the preferred molecular weight ranges from about 2 kDa to about 100 kDa for ease in handling and manufacturing (the term "about" indicating that in preparations of polyethylene glycol, some molecules will weigh more, some less, than the stated molecular weight). Other sizes may be used, depending on the desired therapeutic profile (e.g., the duration of sustained release desired, the effects, if any on biological activity, the ease in handling, the degree or lack of antigenicity and other known effects of polyethylene glycol on a therapeutic protein or variant).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono-, di-, tri-, etc.), the molecular weight of the polymer selected, whether the polymer is branched or unbranched, and the reaction conditions.

The polyethylene glycol molecules (or other chemical moieties) should be attached to the protein with consideration of effects on functional or antigenic domains of the protein. There are a number of attachment methods available to those skilled in the art. See for example, EP 0 401 384, the disclosure of which is hereby incorporated by reference (coupling PEG to G-CSF), see also Malik et al., *Exp. Hematol.*, 20:1028–1035, 1992 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydryl groups may also be used as a reactive group for attaching the polyethylene glycol molecule(s). For therapeutic purposes, attachment at an amino group, such as attachment at the N-terminus or lysine group is preferred. Attachment at residues important for receptor binding should be avoided if receptor binding is desired.

One may specifically desire an N-terminal chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the pKa differences between the e-amino group of the lysine residues and that of the a-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

The present invention contemplates use of derivatives which are prokaryote-expressed GDNF, or variants thereof, linked to at least one polyethylene glycol molecule, as well as use of GDNF, or variants thereof, attached to one or more polyethylene glycol molecules via an acyl or alkyl linkage.

Pegylation may be carried out by any of the pegylation reactions known in the art. See, for example: *Focus on Growth Factors*, 3 (2):4–10, 1992; EP 0 154 316, the disclosure of which is hereby incorporated by reference; EP 0 401 384; and the other publications cited herein that relate to pegylation. The pegylation may be carried out via an acylation reaction or an alkylation reaction with a reactive polyethylene glycol molecule (or an analogous reactive water-soluble polymer).

Pegylation by acylation generally involves reacting an active ester derivative of polyethylene glycol with the GDNF protein or variant. Any known or subsequently discovered reactive PEG molecule may be used to carry out the pegylation of GDNF protein or variant. A preferred activated PEG ester is PEG esterified to N-hydroxysuccinimide. As used herein, "acylation" is contemplated to include without limitation the following types of linkages between the therapeutic protein and a water soluble polymer such as PEG: amide, carbamate, urethane, and the like. See *Bioconjugate Chem.*, 5:133–140, 1994. Reaction conditions may be selected from any of those known in the pegylation art or those subsequently developed, but should avoid conditions of temperature, solvent, and pH that would inactivate the GDNF or variant to be modified.

Pegylation by acylation will generally result in a polypegylated GDNF protein or variant. Preferably, the connecting linkage will be an amide. Also preferably, the resulting product will be substantially only (e.g., >95%) mono-, di- or tri-pegylated. However, some species with higher degrees of pegylation may be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Pegylation by alkylation generally involves reacting a terminal aldehyde derivative of PEG with the GDNF protein or variant in the presence of a reducing agent. Pegylation by alkylation can also result in poly-pegylated GDNF protein or variant. In addition, one can manipulate the reaction conditions to favor pegylation substantially only at the a-amino group of the N-terminus of the GDNF protein or variant (i.e., a mono-pegylated protein). In either case of monopegylation or polypegylation, the PEG groups are preferably attached to the protein via a —CH2-NH— group. With particular reference to the —CH2— group, this type of linkage is referred to herein as an "alkyl" linkage.

Derivatization via reductive alkylation to produce a monopegylated product exploits differential reactivity of different types of primary amino groups (lysine versus the N-terminal) available for derivatization. The reaction is performed at a pH which allows one to take advantage of the pKa differences between the e-amino groups of the lysine residues and that of the a-amino group of the N-terminal residue of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs. In one important aspect, the present invention contemplates use of a substantially homogeneous preparation of monopolymer/GDNF protein (or variant) conjugate molecules (meaning GDNF protein or variant to which a polymer molecule has been attached substantially only (i.e., >95%) in a single location). More specifically, if polyethylene glycol is used, the present invention also encompasses use of pegylated GDNF protein or variant lacking possibly antigenic linking groups, and having the polyethylene glycol molecule directly coupled to the GDNF protein or variant.

Thus, it is contemplated that GDNF protein products to be used in accordance with the present invention may include pegylated GDNF protein or variants, wherein the PEG group(s) is (are) attached via acyl or alkyl groups. As discussed above, such products may be mono-pegylated or poly-pegylated (e.g., containing 2–6, and preferably 2–5, PEG groups). The PEG groups are generally attached to the protein at the a- or e-amino groups of amino acids, but it is also contemplated that the PEG groups could be attached to any amino group attached to the protein, which is sufficiently reactive to become attached to a PEG group under suitable reaction conditions.

The polymer molecules used in both the acylation and alkylation approaches may be selected from among water soluble polymers as described above. The polymer selected should be modified to have a single reactive group, such as an active ester for acylation or an aldehyde for alkylation, preferably, so that the degree of polymerization may be controlled as provided for in the present methods. An exemplary reactive PEG aldehyde is polyethylene glycol propionaldehyde, which is water stable, or mono C1–C10 alkoxy or aryloxy derivatives thereof (see, U.S. Pat. No. 5,252,714). The polymer may be branched or unbranched. For the acylation reactions, the polymer(s) selected should have a single reactive ester group. For the present reductive alkylation, the polymer(s) selected should have a single reactive aldehyde group. Generally, the water soluble polymer will not be selected from naturally-occurring glycosyl residues since these are usually made more conveniently by mammalian recombinant expression systems. The polymer may be of any molecular weight, and may be branched or unbranched.

A particularly preferred water-soluble polymer for use herein is polyethylene glycol. As used herein, polyethylene glycol is meant to encompass any of the forms of PEG that have been used to derivatize other proteins, such as mono-(C1–C10) alkoxy- or aryloxy-polyethylene glycol.

In general, chemical derivatization may be performed under any suitable condition used to react a biologically active substance with an activated polymer molecule. Methods for preparing pegylated GDNF protein or variant will generally comprise the steps of (a) reacting a GDNF protein or variant with polyethylene glycol (such as a reactive ester or aldehyde derivative of PEG) under conditions whereby the protein becomes attached to one or more PEG groups, and (b) obtaining the reaction product(s). In general, the optimal reaction conditions for the acylation reactions will be determined case-by-case based on known parameters and the desired result. For example, the larger the ratio of PEG:protein, the greater the percentage of poly-pegylated product.

Reductive alkylation to produce a substantially homogeneous population of mono-polymer/GDNF protein (or variant) conjugate molecule will generally comprise the steps of: (a) reacting a GDNF protein or variant with a reactive PEG molecule under reductive alkylation conditions, at a pH suitable to permit selective modification of the a-amino group at the amino terminus of said GDNF protein or variant; and (b) obtaining the reaction product(s).

For a substantially homogeneous population of mono-polymer/GDNF protein (or variant) conjugate molecules, the reductive alkylation reaction conditions are those which permit the selective attachment of the water soluble polymer moiety to the N-terminus of GDNF protein or variant. Such reaction conditions generally provide for pKa differences between the lysine amino groups and the a-amino group at the N-terminus (the pKa being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal a-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3–9, preferably 3–6.

Another important consideration is the molecular weight of the polymer. In general, the higher the molecular weight of the polymer, the fewer polymer molecules may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa. The preferred average molecular weight is about 5 kDa to about 50 kDa, particularly preferably about 12 kDa to about 25 kDa. The ratio of water-soluble polymer to GDNF protein or variant will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any GDNF protein or variant having an a-amino group at the amino terminus, and provide for a substantially homogenous preparation of monopolymer/GDNF protein (or variant) conjugate. The term "monopolymer/GDNF protein (or variant) conjugate" is used here to mean a composition comprised of a single polymer molecule attached to a molecule of GDNF protein or GDNF variant protein. The monopolymer/GDNF protein (or variant) conjugate preferably will have a polymer molecule located at the N-terminus, but not on lysine amino side groups. The preparation will preferably be greater than 90% monopolymer/GDNF protein (or variant) conjugate, and more preferably greater than 95% monopolymer/GDNF protein (or variant) conjugate, with the remainder of observable molecules being unreacted (i.e., protein lacking the polymer moiety).

For the present reductive alkylation, the reducing agent should be stable in aqueous solution and preferably be able to reduce only the Schiff base formed in the initial process of reductive alkylation. Preferred reducing agents may be selected from sodium borohydride, sodium cyanoborohydride, dimethylamine borane, trimethylamine borane and pyridine borane. A particularly preferred reducing agent is sodium cyanoborohydride. Other reaction parameters, such as solvent, reaction times, temperatures, etc., and means of purification of products, can be determined case-by-case based on the published information relating to derivatization of proteins with water soluble polymers (see the publications cited herein).

C. GDNF Protein Product Pharmaceutical Compositions

GDNF protein product pharmaceutical compositions typically include a therapeutically effective amount of a GDNF protein product in admixture with one or more pharmaceutically and physiologically acceptable formulation materials. Suitable formulation materials include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial CSF, possibly supplemented with other materials common in compositions for parenteral administration. Neutral buffered saline or saline mixed with serum albumin are further exemplary vehicles.

The primary solvent in a vehicle may be either aqueous or non-aqueous in nature. In addition, the vehicle may contain other pharmaceutically-acceptable excipients for modifying or maintaining the pH, osmolarity, viscosity, clarity, color, sterility, stability, rate of dissolution, or odor of the formulation. Similarly, the vehicle may contain still other pharmaceutically-acceptable excipients for modifying or maintaining the rate of release of GDNF protein product, or for promoting the absorption or penetration of GDNF protein product across the membranes of the eye. Such excipients are those substances usually and customarily employed to formulate dosages for parenteral administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or in a form, e.g., lyophilized, requiring reconstitution prior to administration.

The optimal pharmaceutical formulations will be determined by one skilled in the art depending upon considerations such as the route of administration and desired dosage. See for example, Remington's Pharmaceutical Sciences, 18th Ed. (1990, Mack Publishing Co., Easton, Pa. 18042) pages 1435-1712, the disclosure of which is hereby incorporated by reference. Such formulations may influence the physical state, stability, rate of in vivo release, and rate of in vivo clearance of the present GDNF proteins, variants and derivatives.

Other effective administration forms, such as parenteral slow-release formulations, inhalant mists, or orally active formulations are also envisioned. For example, in a sustained release formulation, the GDNF protein product may be bound to or incorporated into particulate preparations of polymeric compounds (such as polylactic acid, polyglycolic acid, etc.) or liposomes. Hylauronic acid may also be used, and this may have the effect of promoting sustained duration in the circulation. The GDNF protein product pharmaceutical composition also may be formulated for parenteral administration, e.g., by intraocular infusion or injection, and may also include slow-release or sustained circulation formulations. Such parenterally administered therapeutic compositions are typically in the form of a pyrogen-free, parenterally acceptable aqueous solution comprising the GDNF protein product in a pharmaceutically acceptable vehicle. One preferred vehicle is sterile distilled water.

It is also contemplated that certain formulations containing GDNF protein product are to be administered orally. GDNF protein product which is administered in this fashion may be encapsulated and may be formulated with or without those carriers customarily used in the compounding of solid dosage forms. The capsule may be designed to release the active portion of the formulation at the point in the gastrointestinal tract when bioavailability is maximized and pre-systemic degradation is minimized. Additional excipients may be included to facilitate absorption of GDNF protein product. Diluents, flavorings, low melting point waxes, vegetable oils, lubricants, suspending agents, tablet disintegrating agents, and binders may also be employed.

The formulation of topical ophthalmic preparations, including ophthalmic solutions, suspensions and ointments is well known to those skilled in the art (see Remington's Pharmaceutical Sciences, 18th Edition, Chapter 86, pages 1581-1592, Mack Publishing Company, 1990). Other modes of administration are available, including intracameral injections (which may be made directly into the anterior chamber or directly into the vitreous chamber), subconjunctival injections and retrobulbar injections, and methods and means for producing ophthalmic preparations suitable for such modes of administration are also well known.

As used in this application, "extraocular" refers to the ocular surface and the (external) space between the eyeball and the eyelid. Examples of extraocular regions include the eyelid fornix or cul-de-sac, the conjunctival surface and the corneal surface. This location is external to all ocular tissue and an invasive procedure is not required to access this region. Examples of extraocular systems include inserts and "topically" applied drops, gels or ointments which may be used to deliver therapeutic material to these regions. Extraocular devices are generally easily removable, even by the patient.

The following patents disclose extraocular systems which are used to administer drugs to the extraocular regions. Higuchi et al. disclose in U.S. Pat. Nos. 3,981,303, 3,986, 510 and 3,995,635 a biodegradable ocular insert which contains a drug. The insert can be made in different shapes for retention in the cul-de-sac of the eyeball, the extraocular space between the eyeball and the eyelid. Several common biocompatible polymers are disclosed as suitable for use in fabricating this device. These polymers include zinc alginate, poly (lactic acid), poly (vinyl alcohol), poly (anhydrides) and poly (glycolic acid). The patents also describe membrane coated devices with reduced permeation to the drug and hollow chambers holding the drug formulation.

Theeuwes, U.S. Pat. No. 4,217,898, discloses microporous reservoirs which are used for controlled drug delivery. These devices are placed extraocularly in the ocular cul-de-sac. Among the polymer systems of interest are poly (vinylchloride)-co-poly (vinyl acetate) copolymers. Kaufman discloses in U.S. Pat. Nos. 4,865,846 and 4,882, 150 an ophthalmic drug delivery system which contains at least one bio-erodible material or ointment carrier for the conjunctival sac. The patent discloses polymer systems, such as poly (lactide), poly (glycolide), poly (vinyl alcohol) and cross linked collagen as suitable delivery systems.

In the presently described use of GDNF protein product of the treatment of retinal disease or injury it is also advantageous that a topically applied ophthalmic formulation include an agent to promote the penetration or transport of the therapeutic agent into the eye. Such agents are known in the art. For example, Ke et al., U.S. Pat. No. 5,221,696 disclose the use of materials to enhance the penetration of ophthalmic preparations through the cornea.

Intraocular systems are those systems which are suitable for use in any tissue compartment within, between or around the tissue layers of the eye itself. These locations include subconjunctival (under the ocular mucous membrane adjacent to the eyeball), orbital (behind the eyeball), and intracameral (within the chambers of the eyeball itself). In contrast to extraocular systems, an invasive procedure consisting of injection or implantation is required to access these regions.

The following patents disclose intraocular devices. Wong, U.S. Pat. No. 4,853,224, discloses microencapsulated drugs for introduction into the chamber of the eye. Polymers which are used in this system include polyesters and polyethers. Lee, U.S. Pat. No. 4,863,457, discloses a biodegradable device which is surgically implanted intraocularly for the sustained release of therapeutic agents. The device is designed for surgical implantation under the conjunctiva (mucous membrane of the eyeball). Krezancaki, U.S. Pat. No. 4,188,373, discloses a pharmaceutical vehicle which gels at human body temperature. This vehicle is an aqueous suspension of the drug and gums or cellulose derived synthetic derivatives. Haslam et al. disclose in U.S. Pat. Nos. 4,474,751 and 4,474,752 a polymer-drug system which is liquid at room temperature and gels at body temperature. Suitable polymers used in this system include polyoxyethylene and polyoxypropylene. Davis et al. disclose in U.S. Pat. No. 5,384,333 a biodegradable injectable drug delivery polymer which provides long term drug release. The drug composition is made up of a pharmaceutically active agent in a biodegradable polymer matrix, where the polymer matrix is a solid at temperatures in the range 20° to 37° C., and is flowable at temperatures in the range 38° to 52° C. The drug delivery polymer is not limited to the delivery of soluble or liquid drug formulations. For example, the polymer can be used as a matrix for stabilizing and retaining at the site of injection drug-containing microspheres, liposomes or other particulate-bound drugs.

A particularly suitable vehicle for intraocular injection is sterile distilled water in which the GDNF protein product is formulated as a sterile, isotonic solution, properly preserved. Yet another ophthalmic preparation may involve the formulation of the GDNF protein product with an agent, such as injectable microspheres or liposomes, that provides for the slow or sustained release of the protein which may then be delivered as a depot injection. Other suitable means for the intraocular introduction of GDNF protein product includes, implantable drug delivery devices or which contain the GDNF protein product.

The ophthalmic preparations of the present invention, particularly topical preparations, may include other components, for example ophthalmically acceptable preservatives, tonicity agents, cosolvents, wetting agents, complexing agents, buffering agents, antimicrobials, antioxidants and surfactants, as are well known in the art. For example, suitable tonicity enhancing agents include alkali metal halides (preferably sodium or potassium chloride), mannitol, sorbitol and the like. Sufficient tonicity enhancing agent is advantageously added so that the formulation to be instilled into the eye is hypotonic or substantially isotonic. Suitable preservatives include, but are not limited to, benzalkonium chloride, thimerosal, phenethyl alcohol, methylparaben, propylparaben, chlorhexidine, sorbic acid and the like. Hydrogen peroxide may also be used as preservative. Suitable cosolvents include, but are not limited to, glycerin, propylene glycol and polyethylene glycol. Suitable complexing agents include caffeine, polyvinylpyrrolidone, beta-cyclodextrin or hydroxypropyl-beta-cyclodextrin. Suitable surfactants or wetting agents include, but are not limited to, sorbitan esters, polysorbates such as polysorbate 80, tromethamine, lecithin, cholesterol, tyloxapol and the like. The buffers can be conventional buffers such as borate, citrate, phosphate, bicarbonate, or Tris-HCl.

The formulation components are present in concentration that are acceptable to the extraocular or intraocular site of administration. For example, buffers are used to maintain the composition at physiological pH or at slightly lower pH, typically within a pH range of from about 5 to about 8.

Additional formulation components may include materials which provide for the prolonged ocular residence of the extraocularly administered therapeutic agent so as to maximize the topical contact and promote absorbtion. Suitable materials include polymers or gel forming materials which provide for increased viscosity of the ophthalmic preparation. Chitosan is a particularly suitable material as an ocular release-rate controlling agent in sustained release liquid ophthalmic drug formulations (see U.S. Pat. No. 5,422,116, Yen, et. al.) The suitability of the formulations of the instant invention for controlled release (e.g., sustained and prolonged delivery) of an ophthalmic treating agent in the eye can be determined by various procedures known in the art, e.g., as described in *Journal of Controlled Release*, 6:367–373, 1987, as well as variations thereof.

Yet another ophthalmic preparation may involve an effective quantity of GDNF protein product in a mixture with non-toxic ophthalmically acceptable excipients which are suitable for the manufacture of tablets. By dissolving the tablets in sterile water, or other appropriate vehicle, ophthalmic solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc

D. Administration/Delivery of GDNF Protein Product

The GDNF protein product may be administered parenterally via a subcutaneous, intramuscular, intravenous, transpulmonary, transdermal, intrathecal or intracerebral route. For the treatment of ophthalmic conditions, the GDNF protein product may be administered extraocularly or intraocularly, as described above, by topical application, inserts, injection, implants, cell therapy or gene therapy. For example, slow-releasing implants containing the neurotrophic factor embedded in a biodegradable polymer matrix can deliver GDNF protein product. GDNF protein product may be administered extracerebrally in a form that has been modified chemically or packaged so that it passes the blood-brain barrier, or it may be administered in connection with one or more agents capable of promoting penetration of GDNF protein product across the barrier. Similarly, the GDNF protein product may be administered intraocularly, or it may be administered extraocularly in connection with one or more agents capable of promoting penetration or transport of GDNF protein product across the membranes of the eye. The frequency of dosing will depend on the pharmacokinetic parameters of the GDNF protein product as formulated, and the route of administration.

The specific dose may be calculated according to considerations of body weight, body surface area or organ size. Further refinement of the calculations necessary to determine the appropriate dosage for treatment involving each of the above mentioned formulations is routinely made by those of ordinary skill in the art and is within the ambit of tasks routinely performed, especially in light of the dosage information and assays disclosed herein. Appropriate dosages may be ascertained through use of the established assays for determining dosages utilized in conjunction with appropriate dose-response data. It will be appreciated by those skilled in the art that the dosage used in intraocularly administered formulations will be minuscule as compared to that used in a systemic injection or oral administration.

The final dosage regimen involved in a method for treating the above-described conditions will be determined by the attending physician, considering various factors which modify the action of drugs, e.g., the age, condition, body weight, sex and diet of the patient, the severity of any infection, time of administration and other clinical factors. As studies are conducted, further information will emerge regarding the appropriate dosage levels for the treatment of various diseases and conditions.

It is envisioned that the continuous administration or sustained delivery of GDNF may be advantageous for a given treatment. While continuous administration may be accomplished via a mechanical means, such as with an infusion pump, it is contemplated that other modes of continuous or near continuous administration may be practiced. For example, chemical derivatization or encapsulation may result in sustained release forms of the protein which have the effect of continuous presence, in predictable amounts, based on a determined dosage regimen. Thus, GDNF protein products include proteins derivatized or otherwise formulated to effectuate such continuous administration.

GDNF protein product cell therapy, e.g., intraocular implantation of cells producing GDNF protein product, is also contemplated. This embodiment would involve implanting into patients cells capable of synthesizing and secreting a biologically active form of GDNF protein product. Such GDNF protein product-producing cells may be cells that are natural producers of GDNF protein product (analogous to B49 glioblastoma cells) or may be recombinant cells whose ability to produce GDNF protein product has been augmented by transformation with a gene encoding the desired GDNF protein product in a vector suitable for promoting its expression and secretion. In order to minimize a potential immunological reaction in patients being administered GDNF protein product of a foreign species, it is preferred that the natural cells producing GDNF protein product be of human origin and produce human GDNF protein product. Likewise, it is preferred that the recombinant cells producing GDNF protein product be transformed with an expression vector containing a gene encoding a human GDNF protein product. Implanted cells may be encapsulated to avoid infiltration of surrounding tissue. Human or non-human animal cells may be implanted in patients in biocompatible, semipermeable polymeric enclosures or membranes that allow release of GDNF protein product, but that prevent destruction of the cells by the patient's immune system or by other detrimental factors from the surrounding tissue. Such an implant, for example, may be attached to the sclera to produce and release GDNF protein product directly into the vitreous humor.

It is also contemplated that the patient's own cells may be transformed ex vivo to produce GDNF protein product and would be directly implanted without encapsulation. For example, retinal neurons may be retrieved, the cells cultured and transformed with an appropriate vector and transplanted back into the patient's retina where they would produce and release the desired GDNF protein or GDNF protein variant.

GDNF protein product gene therapy in vivo is also envisioned, by introducing the gene coding for GDNF protein product into targeted retinal cells via local injection of a nucleic acid construct or other appropriate delivery vectors. (Hefti, *J. Neurobiol.*, 25:1418–1435, 1994). For example, a nucleic acid sequence encoding a GDNF protein product may be contained in an adeno-associated virus vector or adenovirus vector for delivery to the retinal cells. Alternative viral vectors include, but are not limited to, retrovirus, herpes simplex virus and papilloma virus vectors. Physical transfer, either in vivo or ex vivo as appropriate, may also be achieved by liposome-mediated transfer, direct injection (naked DNA), receptor-mediated transfer (ligand-DNA complex), electroporation, calcium phosphate precipitation or microparticle bombardment (gene gun).

The methodology for the membrane encapsulation of living cells is familiar to those of ordinary skill in the art, and the preparation of the encapsulated cells and their implantation in patients may be accomplished without undue experimentation. See, e.g., U.S. Pat. Nos. 4,892,538, 5,011,472, and 5,106,627, each of which is specifically incorporated herein by reference. A system for encapsulating living cells is described in PCT Application WO 91/10425 of Aebischer et al., specifically incorporated herein by reference. See also, PCP Application WO 91/10470 of Aebischer et al., Winn et al., *Exper. Neurol.*, 113:322–329, 1991, Aebischer et al., *Exper. Neurol.*, 111:269–275, 1991; Tresco et al., *ASAIO*, 38:17–23, 1992, each of which is specifically incorporated herein by reference. Techniques for formulating a variety of other sustained- or controlled-delivery means, such as liposome carriers, bio-erodible particles or beads and depot injections, are also known to those skilled in the art.

It should be noted that the GDNF protein product formulations described herein may be used for veterinary as well as human applications and that the term "patient" should not be construed in a limiting manner. In the case of veterinary applications, the dosage ranges should be the same as specified above.

Other aspects and advantages of the present invention will be understood upon consideration of the following illustrative examples. Example I addresses the effect of GDNF protein product administration in a retinal ganglion cell tissue culture system. Example 2 addresses the use of radiolabelled GDNF protein product to examine potential neuronal populations which can bind, internalize and retrogradely transport GDNF protein product in a receptor-mediated fashion. Example 3 addresses the effect of GDNF protein product administration in a retinal ganglion cell injury model. The results of the retinal ganglion cell injury study demonstrated that GDNF protein product has neurotrophic activity for this neuronal population which was not previously known to be GDNF-responsive.

EXAMPLES

Example 1

GDNF Protein Product Promotes the Survival and Development of Retinal Ganglion Cells In vitro

MATERIALS

The materials used in the following Example were obtained as follows.

Cell Culture Media

High glucose Dulbecco's Modified Eagle's Medium (DMEM; #11965-092), Ham's F12 medium (F12; #11765-021), Leibovitz's L15 medium without sodium bicarbonate (#41300-039); B27 medium supplement (#17504-010), penicillin/streptomycin (#15070-014), L-glutamine (#25030-016), Dulbecco's phosphate-buffered saline (D-PBS; #14190-052), Hank's balanced salt solution with calcium and magnesium salts (HBSS; #24020-026), N-2-hydroxyethylpiperazine-N'-2-ethanesulfonic acid (HEPES; #15630-015), mouse laminin (#23017-015), bovine serum albumin and fraction V (#110-18-017) were all from GIBCO/BRL, Grand Island, N.Y. Heat-inactivated horse serum was from HyClone, Logan, Utah. Poly-L-ornithine hydrobromide (P-3655), bovine insulin (I-5500), human transferrin (T-2252), putrescine (P-6024), progesterone (P-6149) and sodium selenite (S-9133) were all from Sigma Chemical Company, Saint-Louis, Mo. Papain, deoxyribonuclease I (DNAase) and ovalbumin (Papain dissociation system) were from Worthington Biochemicals, Freehold, N.J. Falcon sterile 96-well microplates (#3072), tissue culture plastic ware and polypropylene centrifuge tubes were from Beckton-Dickinson, Oxnard, Calif. Nitex 20 µm nylon mesh (#460) was from Tetko, Elmsford, N.Y. The 4" dissecting forceps and 4" dissecting scissors were from Roboz Surgical, Washington, D.C.

Antibodies and Related Reagents

Mouse/rat monoclonal antibodies against mouse Thy-1,2 were from Boehringer-Mannheim (Indianapolis, IN). Rabbit polyclonal anti-rat and anti-mouse IgG antibodies, biotinylated horse anti-mouse IgG and peroxidase-conjugated avidin/biotin complex (ABC Elite; kit PK-6100) were from Vector Laboratories, Burlingame, Calif. 3',3'-diaminobenzidine was from Cappel Laboratories, West Chester, Pa. Superblock blocking buffer in PBS (#37515) was from Pierce, Rockford, Ill. Triton X-100 (X100), Nonidet P-40 (N6507) and hydrogen peroxide (30%, v/v; H1009) were from Sigma. All other reagents were obtained from Sigma Chemical Company (Saint-Louis, Mo.), unless otherwise specified.

METHODS

Preparation of Media

A basal medium was prepared as a 1:1 mixture of DMEM and F12 medium, and was supplemented with B27 medium supplement added as a 50-fold concentrated stock solution. The B27 medium supplement consists of biotin, L-carnitine, corticosterone, ethanolamine, D(+)-galactose, reduced glutathione, linoleic acid, linolenic acid, progesterone, putrescine, retinyl acetate, selenium, T3 (triodo-1-thyronine, DL-alpha-tocopherol; vitamin E), DL-alpha-tocopherol acetate, bovine serum albumin, catalase, insulin, superoxide dismutase and transferrin. L-glutamine was added at a final concentration of about 2 mM, penicillin at about 100 IU/l, and streptomycin at about 100 mg/l. Heat-inactivated horse serum was added to a final concentration of about 2.5 percent, D-glucose was added to a final concentration of about 5 g/l, HEPES buffering agent was added to a final concentration of about 20 mM, bovine insulin was added to a final concentration of about 2.5 mg/ml, and human transferrin was added to a final concentration of about 0.1 mg/ml. After mixing, the pH was adjusted to about 7.3 and the medium was kept at 4° C. The media were prepared fresh just before use in order to minimize inter-experimental variations. Plastic pipettes and containers were used throughout to minimize protein adsorption.

GDNF Protein Product Solutions

Purified human recombinant GDNF protein products were prepared as 1 mg/ml solutions in D-PBS (phosphate buffered saline prepared with distilled water) containing five percent bovine serum albumin. The solutions were stored at −85° C. in aliquots. Serial dilutions were prepared in 96-well microplates. Ten microliters of ten-fold concentrated GDNF protein product solutions were added to cell cultures containing culture medium (90 µl). Control cultures received D-PBS with 5 percent albumin (10 µl). The GDNF protein product treatments were initiated one hour after cells were seeded and, in some instances, repeated every other day.

Culture Substratum

To encourage optimal attachment of retinal ganglion cells on substratum and neurite outgrowth, the microliter plate surfaces (the culture substratum) were modified by sequential coating with poly-L-ornithine followed by laminin in accordance with the following procedure. The plate surfaces were completely covered with a 0.1 mg/ml sterile solution of polyornithine in 0.1M boric acid (pH 8.4) for at least one hour at room temperature, followed by a sterile wash with Super-Q water. The water wash was then aspirated and a 1 µg/ml solution of mouse laminin in PBS was added and incubated at 37° C. for two hours. These procedures were conducted just before using the plates in order to ensure reproducibility of the results.

Preparation of Rat Retinal Ganglion Cell Cultures

Seven-day-old Sprague-Dawley rat pups (obtained from Jackson Laboratories, Bar Harbor, Me.) were killed by decapitation and the eyes were dissected sterilely into L15 medium (without sodium bicarbonate). A maximum of 24 eyes were processed per experiment. The eyes were hemisected, and the lens and vitreous were removed. The neural retinas were carefully removed and dissected free of the pigment epithelium, cut into small (about 1 square mm or less) fragments and placed into ice-cold D-PBS. The cells were collected, and then transferred into 10 ml dissociation medium (120 units papain and 2000 units DNAase in HBSS). The cells were incubated for 45 minutes at about 37° C. on a rotary platform shaker at about 200 rpm. The cells were then dispersed by trituration through fire-polished Pasteur pipettes, sieved through a 20 µm Nitex nylon mesh to discard undissociated tissue, and centrifuged for five minutes at 200×g using an IEC clinical centrifuge. The resulting cell pellet was resuspended into HBSS containing ovalbumin and about 500 units DNAase, layered on top of a four percent ovalbumin solution (in HBSS) and centrifuged for about 10 minutes at 500×g. The final pellet was resuspended into DMEM/F12 supplemented with 20% fetal bovine serum at a concentration of $10^7$ cells/ml, and retinal ganglion cells were purified by immunopanning according to a previously described method (Lehwalder et al., *J. Neurosci. Res.*, 24:329–337, 1989).

For panning, 35-mm tissue culture plastic dishes were precoated with an anti-mouse IgG antibody (diluted 1:100 in PBS) for two hours at room temperature, washed three times with PBS containing 1% bovine serum albumin and then incubated with a mouse monoclonal antibody against Thy-1,2 (diluted 1:100). After rinsing the dishes with DMEM/F12, about one milliliter of the retinal cell suspension was incubated on the pretreated culture dishes for one hour at room temperature. The non-adhering cells were dislodged by repeated washings with culture medium until only firmly adherent cells remained. The bound cells were harvested using a rubber policeman and resuspended in complete culture medium (as described above). The cell concentration was then adjusted to about 11,000 cells/ml and the cell suspension was seeded in 90 µl at a density of about 1,000 cells per 6-mm well aliquots into 96-well microplates previously coated with polyornithine and laminin of medium. Attachment of cells occurred rapidly, and the plating efficiency was about 50 percent.

Immunohistochemistry of Retinal Ganglion Cells

To characterize rat retinal ganglion cells, an indirect immunoperoxidase method described by Louis et al. (*J. Pharmacol. Exp. Therap.*, 262:1274–1283, 1992; *Science*, 259:689–692, 1993) was used, with slight modifications as follows. Cultures of retinal ganglion cells were fixed for about 30 minutes at room temperature with four percent paraformaldehyde in D-PBS, pH 7.4, followed by three washes in D-PBS (200 µl per 6-mm well). The fixed cultures were then incubated in Superblock blocking buffer in PBS, containing one percent Nonidet P-40 to increase the penetration of the antibodies. The mouse monoclonal anti-Thy-1 antibodies (Boehringer-Mannheim) were then applied at a dilution of between 1:100–1:400 in the same buffer, and the cultures were incubated for one hour at 37° C. on a rotary shaker. After three washes with D-PBS, the retinal ganglion cell-bound antibodies were detected using horse-anti-mouse biotinylated IgG (Vectastain kit from Vector Laboratories, Burlingame, Calif.) at about a 1:500 dilution: these secondary antibodies were incubated with the cells for about one hour at 37° C., the cells were then washed three times with D-PBS. The secondary antibodies were then labeled with an avidin-biotin-peroxidase complex diluted at 1:500, and the cells were incubated for about 45 minutes at 37° C. After three more washes with D-PBS, the labeled cell cultures were reacted for 5–20 minutes in a solution of 0.1M Tris-HCl, pH 7.4, containing 0.04% 3',3'-diaminobenzidine-(HCl)4, 0.06 percent $NiCl_2$ and 0.02 percent hydrogen peroxide.

Determining Retinal Ganglion Cell Survival

After various times in culture (24 hours, 3 days and 6 days), rat retinal ganglion cell cultures were fixed, processed and immunostained for Thy-1,2 as described above, and the cultures were then examined with bright-light optics at 200× magnification. All the Thy-1,2-positive neurons present in a 6-mm well were counted. Viable retinal ganglion cells were characterized as having a large (30–40 µm diameter), regularly-shaped cell body, with about three long neuritic processes, one of which being an axon. Retinal ganglion cells showing signs of degeneration, such as having irregular, vacuolated perikarya or fragmented neurites, were excluded from the counts (most of the degenerating retinal ganglion cells, however, detached from the culture substratum). Cell numbers were expressed either as cells/6-mm well or as the fold-change relative to control cell density.

RESULTS

Cultures of purified rat retinal ganglion cells were used to demonstrate the effect of GDNF protein product on survival and morphological maturation. The retinal ganglion cells were purified from seven-day old rat retinas by immuno-panning on plastic surfaces coated with anti-Thy-1,2 antibodies. In the rat retina, the Thy-1 antigen is known to be localized on retinal ganglion cells (Leifer et al., *Exp. Neurol.*, 113:386–390, 1991). Pure cultures of retinal ganglion cells were then established by seeding the resulting pure population of retinal ganglion cells cultures into polyornithine-laminin-coated microplates at a density of about 1,000 per 6-mm well in DMEM/F12 supplemented with B27 medium supplement, 2.5 percent heat-inactivated horse serum, D-glucose, HEPES, insulin and transferrin. Retinal ganglion cells were identified by the presence of Thy,1,2 immunoreactivity. This method resulted in a relatively low yield of retinal ganglion cells (about 5,000 cells per retina), but a high degree of purity (about 90% of Thy-1,2-positive cells).

Rat retinal ganglion cell cultures were evaluated for the effect of GDNF protein product administration on survival and morphological maturation. Cultures of retinal ganglion cells were treated with human recombinant GDNF protein product (three-fold serial dilutions ranging from 10 ng/ml to 1 pg/ml). The cultures were fixed after 24 hours, 3 days and 6 days in vitro, the cultures were fixed with 4% paraformaldehyde and immunostained for Thy-1,2. In cultures that were not treated with GDNF protein product, only about 32±4 percent (n=6) of the seeded retinal ganglion cells survived after 24 hours in culture. About 11±3 percent (n=6) of the original seed of retinal ganglion cells were present after three days, and only 3±2 percent (n=3) were still found after six days in culture. Treatment of the cultures with *E. coil*-expressed recombinant human GDNF protein product resulted in an about 2.5-fold increase in the number of viable retinal ganglion cells after 24 hours in culture (80±6, n=6). After three days in the presence of GDNF protein product, about 50±5 percent (n=5) of the original number of retinal ganglion cells survived (4.5-fold increase over control) and after six days, about 39±4 percent (n=3) were still viable (9.6-fold increase over control). The effect of GDNF protein product on retinal ganglion cell survival after three days/n vitro was maximal at about 300 pg/ml, with an ED50 of about 30 pg/ml.

In addition to promoting retinal ganglion cell survival, the addition of the GDNF protein product also stimulated their morphological development. Treatment with GDNF protein product resulted in an increase in the size of the retinal ganglion cells' soma and in the length and branching of their neuritic processes. After three days in vitro, many retinal ganglion cells in GDNF-treated cultures bore neurites 500 to 1000 µm in length, while the longest neurites seen in control cultures were less than 300 µm in length.

Example 2

Retrograde Transport of GDNF Protein Product in Retinal Ganglion Cells

In this experiment, $^{125}$I-radiolabelled GDNF protein product was injected into adult rat brains to identify potential neuronal populations which can bind, internalize and retrogradely transport GDNF in a receptor-mediated fashion. The GDNF protein product tested was recombinant human [Met$^-$1]GDNF and was produced by expression in *E. coli* as generally described in Examples 6B and 6C of WO93/06116. The purified [Met$^{-1}$]GDNF was iodinated using the lactoperoxidase technique and separated from free $^{125}$I using G-25 Sephadex quick spin columns as described in Yan et al., *J. Neurobiol.*, 24:1555–77, 1993. Adult Sprague-Dawley rats were anesthetized with a cocktail of 43 mg/ml ketamine hydrochloride, 8.6 mg/ml of xylazine and 1.43 mg/ml of acepromazine, at a dose of 0.7 ml/kg body weight. In one group of 6 rats, either 5 µl of $^{125}$I-[Met$^{-1}$]GDNF (containing a total of 4–5×10$^6$ cpm radioactivity) or 5 µl of $^{125}$I-[Met$^-$1]GDNF with a 111-fold excess of unlabeled [Met$^{-1}$]GDNF in PBS/BSA were injected into the right lateral ventricle stereotaxically with a 5-µl Hamilton syringe. In a second group of 6 rats, 1 µl of $^{125}$I-[Met$^{-1}$]GDNF with or without 111-fold excess unlabeled [Met$^{-1}$]GDNF was injected into the middle of the right striatum. In a third group of 6 rats, 1 µl of $^{125}$I-[Met$^{-1}$]GDNF with or without 111-fold excess unlabeled [Met$^{-1}$]GDNF was injected into the superior colliculus. The injection rate was 0.1 µl per 15 seconds for all injections.

After 20–24 hours survival time, the animals were sacrificed and perfused with 4% paraformaldehyde and 1% glutaraldehyde in 0.1M sodium phosphate buffer, pH 7.2. The brains were removed and cryoprotected. The rats with the superior colliculus injection were sacrificed, and their eyes were removed and immersion-fixed with the same fixative. The radioactivity of the eyes was counted in a scintillation counter. Frozen coronal sections of the brains at a thickness of 25 μm were cut on a sliding microtome, and 10 μm sections of the eyes were cut with a cryostat. The sections were mounted on glass slides and dipped in Kodak NTB-3 emulsion. Exposure times varied from 15 to 30 days. The slides were then developed, counterstained with toluidine blue and examined under a microscope.

After intra-striatal or intracerebroventricular (ICV) injection into the central nervous system (CNS), uptake and transport of $^{125}$I-[Met$^{-1}$]GDNF was observed in dopaminergic neurons in the substantia nigra and ventral tegmental area. Co-injection of excess unlabeled [Met$^1$]GDNF could completely block the neuronal labeling by either ICV or intra-striatal injection of $^{125}$I-[Met$^{-1}$]GDNF. These dopaminergic neurons, which are biologically responsive to GDNF, were expected to express functional GDNF receptors which are capable of uptake and retrograde transport. The specific labeling of these dopaminergic neurons with ICV and intra-striatally injected $^{125}$I-[Met$^{-1}$]GDNF thus served as a good positive control.

In addition, low-level labeling of neurons was observed in the central linear nucleus of raphe and dorsal nucleus of raphe after both intra-striatal and ICV injection. The uptake of the labeled [Met$^{-1}$]GDNF was blocked by co-injection of an excess of unlabeled [Met$^{-1}$]GDNF, indicating that the uptake occurred via a receptor-mediated mechanism. No labeling of neurons in the other neighboring raphe nuclei or in any other neuronal populations in the entire adult rat brain was observed after intra-striatal or ICV injection.

In an attempt to find other neuronal populations, such as in the eye, which have no access to the ventricular system but may be able to take up and retrogradely transport GDNF, $^{125}$I-[Met$^{-1}$]GDNF was injected into the superior colliculus. The radioactivity observed upon direct counting of the eye selectively accumulated in the contralateral eye but not the ipsilateral eye. This selectivity is presumably due to the cross-projection of retinal ganglion cells to the contralateral superior colliculus. The accumulation of radioactivity could be blocked by co-injection of an excess of unlabeled [Met$^{-1}$]GDNF. Autoradiograms of the cross-section of these eyes showed that the radioactivity was specifically associated with the retinal ganglion cells. The results showed that $^{125}$I-[Met$^{-1}$]GDNF was selectively transported to the contralateral but not ipsilateral retinal ganglion cells via a receptor-mediated mechanism.

Example 3

Promotion of Retinal Ganglion Cell Survival via Administration of GDNF Protein Product In this experiment, the effect of GDNF protein product or vehicle administration in an animal model of optic nerve axotomy was evaluated by a method described in Mansour-Robaey et al., *Proc, Natl. Acad. Sci.*, 91:1632–1636, 1994. In this model, axotomy of the optic nerve causes a reproducible retinal ganglion cell death in adult rats. Retinal ganglion cells were pre-labeled by applying Fluorogold soaked Gelfoam to the surface of both left and right superior colliculi of female adult Sprague-Dawley rats. One week after Fluorogold application (day 0), the right optic nerve was transected 0.5 mm from the eye (n=3–6, for each treatment). The left eye served as the internal control showing labeling of retinal ganglion cells.

Animals were treated with 1 μl of either [Met$^{-1}$]GDNF (1 mg/ml in PBS) or cytochrome c as a negative control via intraocular injection into the right eye at day 0 or day 7. The effect of axotomy and drug treatment was examined at day 7 or day 14, as shown in Table 2, after the optic nerve transection.

TABLE 2

| Group | Injection Date | Examination Date |
|-------|----------------|------------------|
| 1     | 0              | 7                |
| 2     | 0              | 14               |
| 3     | 0, 7           | 14               |

Eyes were immersion fixed with 4% paraformaldehyde for one hour. The orientation of the retina was marked. The retinas were dissected, whole mounted on glass slides, examined and photographed under a fluorescent microscope. The number of retinal ganglion cells was then counted in the photographs. It was observed that axotomy with or without cytochrome c (the negative control) resulted in a dramatic decrease in the number of labeled retinal ganglion cells at 7 days, which further declined at day 14. [Met$^{-1}$]GDNF treatment at day 0 resulted a clear saving of retinal ganglion cells at day 7 and day 14. Two treatments with 1 μl of [Met$^{-1}$]GDNF at day 0 and day 7 resulted in the further enhancement of retinal ganglion cell survival at day 14. These results demonstrate that the retinal ganglion cells are responsive to GDNF and that treatment with GDNF protein product increases the survival of injured retinal ganglion cells, which are the main population of neurons damaged in glaucoma.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

---

What is claimed is:

1. A method for treating injury or degeneration of retinal ganglion cells comprising administering to a subject suffering from such retinal ganglion cell injury or degeneration a therapeutically effective amount of a glial cell line-derived neurotrophic factor (GDNF) protein product.

2. The method of claim 1 wherein the injury or degeneration of retinal ganglion cells is associated with glaucoma.

3. The method of claim 1 wherein the GDNF protein product is the amino acid sequence set forth in SEQ ID NO:1 or a variant or a derivative thereof.

4. The method of claim 3 wherein the GDNF protein product has the amino acid sequence set forth in SEQ ID NO:1.

5. The method of claim 3 wherein the GDNF protein product is [Met$^{-1}$]GDNF.

6. The method of claim 3 wherein the derivative comprises a water soluble polymer.

7. The method of claim 6 wherein the water soluble polymer is polyethylene glycol.

8. The method of claim 1 wherein the GDNF protein product is administered at a dose of about 1 µg/kg/day to about 100 mg/kg/day.

9. The method of claim 1 wherein the GDNF protein product is administered as a sustained-release pharmaceutical composition.

10. The method of claim 1 wherein the GDNF protein product is administered as a topical, oral or parenteral pharmaceutical composition.

11. The method of claim 1 wherein the GDNF protein product is administered by cell therapy or gene therapy means wherein cells have been modified to produce and secrete the GDNF protein product.

12. The method of claim 11 wherein the cells have been modified ex vivo.

13. The method of claim 11 wherein the cells have been modified in vivo.

14. The method of claim 2 further comprising administering to the patient an effective amount of a second therapeutic agent for glaucoma.

15. The method of claim 14 wherein the second therapeutic agent is selected from the group consisting of parasympathomimetic agents, beta-adrenergic blockers, sympathomimetics, indirect parasympathomimetics and carbonic anhydrase inhibitors.

16. A method for treating injury or degeneration of the optic nerve comprising administering to a subject suffering from such injury or degeneration a therapeutically effective amount of a glial cell line-derived neurotrophic factor (GDNF) protein product to promote the survival or regeneration of retinal ganglion cell axons forming the optic nerve.

17. The method of claim 16 wherein injury or degeneration of the optic nerve is associated with conditions affecting the optic nerve head selected from the group consisting of glaucoma, papilledema, papillitis and ischemia.

18. The method of claim 16 wherein the GDNF protein product is the amino acid sequence set forth in SEQ ID NO:1 or a variant or a derivative thereof.

19. The method of claim 18 wherein the GDNF protein product has the amino acid sequence set forth in SEQ ID NO:1.

20. The method of claim 18 wherein the GDNF protein product is [Met$^{-1}$]GDNF.

* * * * *

UNITED STATES PATENT AND TRADEMARK OFFICE
CERTIFICATE OF CORRECTION

PATENT NO. : 5,641,749
DATED : June 24, 1997
INVENTOR(S) : Qiao Yan and Jean-Claude Louis It is certified that error appears in the above-identified patent and that said Letters Patent is hereby corrected as shown below:

On the title page: Item [54] and Column 1, line 1,
   change "NEUROTHROPHIC" to --NEUROTROPHIC--.

column 1, Other Publications, line 2, change "Midgrain Depaminergic" to --Midbrain Dopaminergic--.

line 3, change "EMSO" to --EMBO--.

line 5, change "Tranplantation" to --Transplantation--.

Column 1, line 3, change "NEUROTHROPHIC" to --NEUROTROPHIC--.

line 19, change "1979" to --1978--.

Column 2, line 16, change "Oppenheimet" to --Oppenheim et--.

Column 9, line 67, change "Lle" to --Ile--.

Column 20, line 21, change "PCP" to --PCT--.

Column 24, line 21, change "days/n" to --days in--.

Column 25, line 12, change "[Met$^1$]" to --[Met$^{-1}$]--.

Signed and Sealed this

Ninth Day of December, 1997

Attest:

BRUCE LEHMAN

*Attesting Officer*    *Commissioner of Patents and Trademarks*